US006420574B2

(12) United States Patent
Petersen et al.

(10) Patent No.: US 6,420,574 B2
(45) Date of Patent: Jul. 16, 2002

(54) METHOD FOR THE PREPARATION OF CITALOPRAM

(75) Inventors: Hans Petersen, Vanløse; Michael Harold Rock, Hvidovre; Haleh Ahmadian, Solrød Strand, all of (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/794,762

(22) Filed: Feb. 26, 2001

(30) Foreign Application Priority Data

Feb. 24, 2000 (DK) .......................... 2000 00296
Mar. 13, 2000 (DK) .......................... 2000 00401

(51) Int. Cl.[7] ..................... C07D 307/78; A61K 31/34
(52) U.S. Cl. ........................ 549/467; 514/469
(58) Field of Search ..................... 514/469; 549/467

(56) References Cited

U.S. PATENT DOCUMENTS

| 3,467,675 A | 9/1969 | Petersen et al. ......... 260/346.2 |
| 4,136,193 A | 1/1979 | Bogeso et al. ............. 424/285 |
| 4,650,884 A | 3/1987 | Bogese ..................... 549/647 |
| 4,943,590 A | 7/1990 | Boegesoe et al. .......... 415/469 |
| 5,296,007 A | 3/1994 | Tanaka et al. ............. 514/465 |
| 6,020,501 A | 1/2000 | Massonne et al. ......... 549/307 |
| 6,028,204 A | 2/2000 | Massonne et al. ......... 549/307 |
| 6,229,026 B1 | 5/2001 | Petersen .................... 549/467 |
| 6,258,842 B1 | 7/2001 | Petersen et al. ........... 514/469 |
| 6,291,689 B1 | 9/2001 | Petersen et al. ........... 549/467 |

FOREIGN PATENT DOCUMENTS

| EP | 0 171 943 | 2/1988 | |
| EP | 1 095 926 | 5/2001 | ........... C07C/33/46 |
| WO | WO 98/19511 | 4/1998 | |
| WO | WO 98/19512 | 4/1998 | |
| WO | WO 98/19513 | 5/1998 | |
| WO | 99/30548 | 6/1999 | |
| WO | 00/11926 | 3/2000 | |
| WO | 00/12044 | 3/2000 | |
| WO | 00/13648 | 3/2000 | |
| WO | 00/23431 | 4/2000 | ........ C07D/307/87 |
| WO | 00/39112 | 7/2000 | ........ C07D/307/87 |
| WO | 00/44738 | 8/2000 | ........ C07D/307/88 |

OTHER PUBLICATIONS

Bigler, Allan J. et al., "Quantitative structure–activity relationships in a series of selective 5–HT uptake inhibitors," *Eur. J. Med. Chem.—Chimica Therapeutica*, 12 3:289–295 (May–Jun. 1977).

Moltzen, Ejner K. et al., "σ Ligands with Subnanomolar Affinity and Preference for the $\sigma_2$ Binding Site 2. Spiro-–Joined Benzofuran, Isobenzofuran, and Benzopyran Piperidines," *J. Med. Chem.* 38:2009–2017 (1995).

(List continued on next page.)

*Primary Examiner*—Amelia Owens
(74) *Attorney, Agent, or Firm*—Darby & Darby

(57) ABSTRACT

The present invention relates to a method for the preparation of citalopram comprising reaction a compound of formula (I)

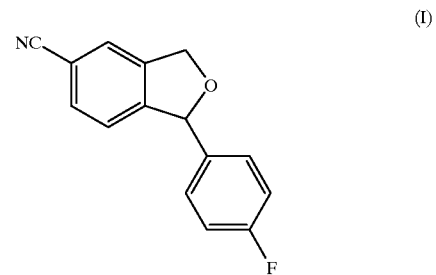

with a compound having the formula

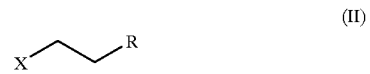

wherein X is a suitable leaving group and R is —CH$_2$—O—Pg, —CH$_2$—NPg$_1$Pg$_2$, —CO—N(CH$_3$)$_2$, —CH(OR$^1$)(OR$^2$), —C(OR$^4$)(OR$^5$)(OR$^6$), —COOR$^3$, —CH$_2$—CO—NH$_2$, —CH=CHR$^7$ and —CONHR$^8$, wherein Pg is a protection group for an alcohol group, Pg$_1$ and Pg$_2$ are protection groups for an amino group, R$^1$ and R$^2$ are independently selected from alkyl, alkenyl, alkynyl and optionally alkyl substituted aryl or aralkyl groups or R$^1$ and R$^2$ together form a chain of 2 to 4 carbon atoms, each of R$^3$, R$^4$, R$^5$, R$^6$ and R$^7$ are independently selected from alkyl, alkenyl, alkynyl and optionally alkyl substituted aryl or aralkyl and R$^8$ is hydrogen or methyl;

to form a compound of the formula

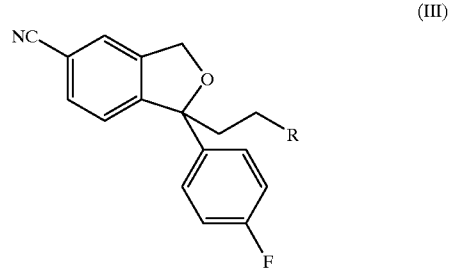

wherein R is as defined above; followed by conversion of the R group and isolation of citalopram base or a pharmaceutically acceptable salt thereof.

18 Claims, No Drawings

OTHER PUBLICATIONS

Perregaard, Jens et al., "σ Ligands with Subnanomolar Affinity and Preference for the $\sigma_2$ Binding Site 1. 3–(ω–Aminoalkyl)–1H–indoles," *J. Med. Chem.* 38:1998–2008 (1995).

U.S. Patent Application Serial No. 09/692,653, filed Oct. 19, 2000 (Petersen, et al.).

U.S. Patent Application Serial No. 09/794,755, filed Feb. 26, 2001 (Petersen, et al.).

U.S. Patent Application Serial No. 09/830,109, filed Oct. 19, 1999 (Dall'Astra et al.).

U.S. Patent Application Serial No. 09/891,874, filed Oct 25, 1999 (Rock, et al.).

U.S. Patent Application Serial No. 09/888, 067, filed Dec. 22, 1999 (Petersen, et al.).

U.S. Patent Application Serial No. 09/917,180, filed Jan. 26, 2000 (Weber).

U.S. Patent Application Serial No. 09/977,920, filed Apr. 14, 1999 (Petersen).

METHOD FOR THE PREPARATION OF CITALOPRAM

The present invention relates to a method for the preparation of the well-known antidepressant drug citalopram,1-[3-(dimethylamino)propyl]-1-(4fluorophenyl)-1,3-dihydro-5-isobenzofurancarbonitrile.

BACKGROUND OF THE INVENTION

Citalopram is a well-known antidepressant drug that has now been on the market for some years and has the following structure:

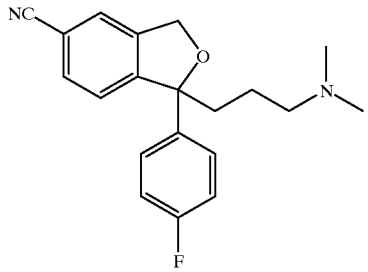

It is a selective, centrally acting serotonin (5-hydroxytryptamine; 5-HT) reuptake inhibitor, accordingly having antidepressant activities. The antidepressant activity of the compound has been reported in several publications, eg. J. Hyttel *Prog. Neuro-Psychopharmacol. & Biol. Psychiat.* 1982, 6, 277–295 and A. Gravem *Acta Psychiatr. Scand.* 1987, 75, 478–486. The compound has further been disclosed to show effects in the treatment of dementia and cerebrovascular disorders, EP-A-474580.

Citalopram was first disclosed in DE 2,657,013, corresponding to U.S. Pat No. 4,136,193. This patent publication describes the preparation of citalopram by one method and outlines a further method which may be used for preparing citalopram.

According to the process described, the corresponding 1-(4fluorophenyl)-1,3dihydro-5-isobenzofurancarbonitrile is reacted with 3-(N,N-dimethylamino)propyl-chloride in the presence of methylsulfinylmethide as condensing agent. The starting material was prepared from the corresponding 5-bromo derivative by reaction with cuprous cyanide.

International patent application No. WO 98/019511 discloses a process for the manufacture of citalopram wherein a (4- (cyano, alkyloxycarbonyl or alkylamninocarbonyl)-2-hydroxymethylphenyl-(4-fluorophenyl)methanol compound is subjected to ring closure. The resulting 5-(alkyloxycarbonyl or alkylaminocarbonyl)-1-(4fluorophenyl)-1,3-dihydroisobenzofuran is converted to the corresponding 5-cyano derivative and the 5-cyano derivative is then alkylated with a (3-dimethylamino) propylhalogenide in order to obtain citalopram.

It has now, surprisingly, been found that citalopram may be manufactured by a novel favourable process where 5-cyano-1-(4-fluorophenyl)-1,3-dihydroisobenzofuran is alkylated with a compound which may be converted to a dimethylaminopropyl group.

The alkylation process according to the invention is particularly advantageous because the formation of by-products by polymerisation of the alkylating agent is avoided whereby a reduction in the amount of alkylating reagent used is made possible. In addition, the process of the invention provides high yields.

SUMMARY OF THE INVENTION

The present invention relates to a method for the preparation of citalopram comprising reaction of a compound of formula (I)

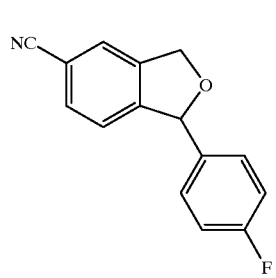

with a compound having the formula

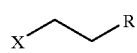

wherein X is a suitable leaving group and R is —$CH_2$—O—Pg, —$CH_2$—$NPg_1Pg_2$, —$CH_2$—$NMePg_1$, —CO—N$(CH_3)_2$, —CH($OR^1$)($OR^2$), —C($OR^4$)($OR^5$)($OR^6$), —$COOR^3$, —$CH_2$—CO—$NH_2$, —CH=$CHR^7$ or —CO—$NHR^8$ wherein Pg is a protection group for an alcohol group, $Pg_1$ and $Pg_2$ are protection groups for an amino group, $R^1$ and $R^2$ are independently selected from alkyl, alkenyl, alkynyl and optionally alkyl substituted aryl or aralkyl groups or $R^1$ and $R^2$ together form a chain of 2 to 4 carbon atoms, $R^3$, $R^4$, $R^5$, $R^6$ and $R^7$ are independently selected from alkyl, alkenyl, alkynyl and optionally alkyl substituted aryl or aralkyl and $R^8$ is hydrogen or methyl; to form a compound of the formula

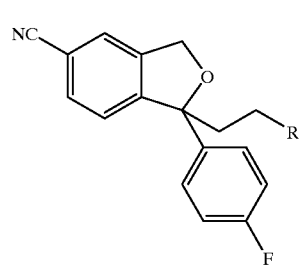

wherein R is as defined above; followed by conversion of the group R to a dimethylaminomethyl group and isolation of citalopram in the form of the base or as a pharmaceutically acceptable salt thereof.

In a first embodiment of the invention, the compound of formula (I) is reacted with a compound of formula (II) wherein R is —$CH_2$—O—Pg, wherein Pg is a protection group for an alcohol group, followed by removal of the protection group to form the corresponding alcohol of the formula

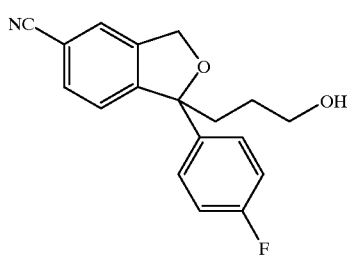

(IV)

The alcohol group is then converted to a feasible leaving group such as halogen or —O—SO$_2$—R$^0$ wherein R$^0$ is alkyl, or optionally alkyl substituted aryl or aralkyl, and the resulting compound is then a) reacted with dimethylamin or a metal salt thereof to form citalopram,
b) reacted with methylamin to form a compound of formula (XII) below followed by reductive amination to form citalopram, or
c) reacted with an azide followed by reduction to form the corresponding amino compound of formula (VI) below and thereafter methylation or reductive amination to form citalopram.

In a second embodiment, the compound of formula (I) is reacted with a compound of formula (II) wherein R is —CO—N(CH$_3$)$_2$, followed by reduction of the resulting compound of the formula

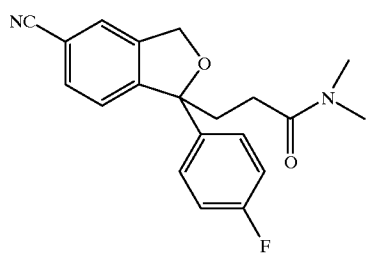

(V)

to form citalopram.

In a third embodiment, the compound of formula (I) is reacted with a compound of formula (II) wherein R is —CH$_2$—N(Pg$_1$)(Pg$_2$) where Pg$_1$ or Pg$_2$ are protection groups for an amino group and thereafter removal of the protection groups to form a compound of formula

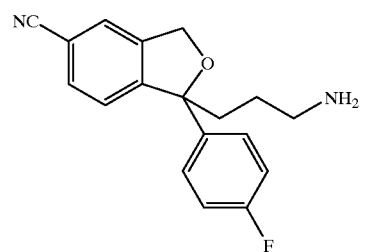

(VI)

followed by methylation of the free amino group or reductive amination to form citalopram.

In a fourth embodiment, citalopram may be prepared by reaction of a compound of formula (I) with a compound of formula (II) wherein R is —CH(OR$^1$)(OR$^2$) or —C(OR$^4$)(OR$^5$)(OR$^6$) where R$^1$, R$^2$, R$_4$, R$^5$ and R$^6$ are as defined above to form a compound of the formula (VIIa) or (VIIb)

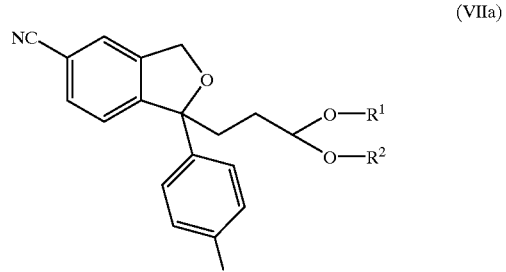

(VIIa)

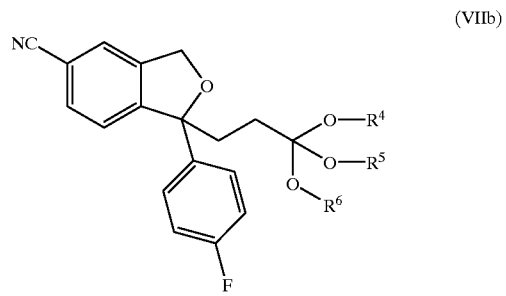

(VIIb)

wherein R$^1$, R$^2$, R$^4$, R$^5$ and R$^6$ are as defined above, followed by deprotection of the compound of formula (VIIa) or (VIIb) and consecutively reductive amination of the resulting aldehyde with dimethylamin to form citalopram.

In a fifth embodiment, citalopram may be prepared by reaction of a compound of formula (I) with a compound of formula (II) wherein R is —COOR$^3$ and R$^3$ is as defined above to form a compound of the formula

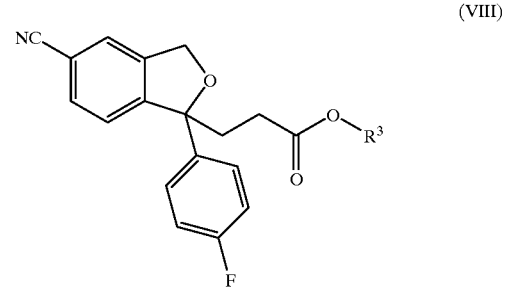

(VIII)

wherein R$^3$ is as defined above, which is then converted to an amide of formula (V) or an alcohol of formula (IV) which is converted to citalopram as described above.

In a sixth embodiment, the invention relates to a method for the preparation of citalopram wherein a compound of formula (I) is reacted with a compound of formula (II) wherein R is —CH$_2$—CONH$_2$ to form a compound of formula

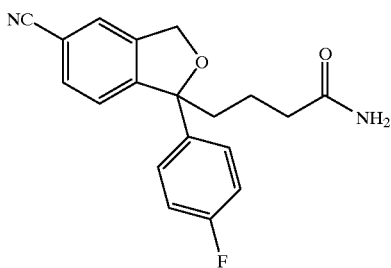

(IX)

which is treated with hypohalide to form a compound of formula

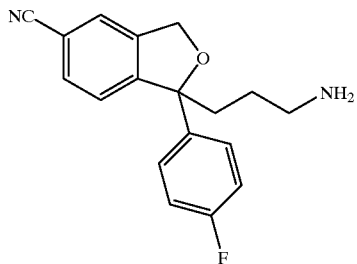

(VI)

followed by methylation of the free amino group or reductive amination to form citalopram.

In a seventh embodiment, the invention relates to a method for the preparation of citalopram by reaction of a compound of formula (I) with a compound of formula (II) wherein R is —CH=CHR$^7$ to form a compound of formula

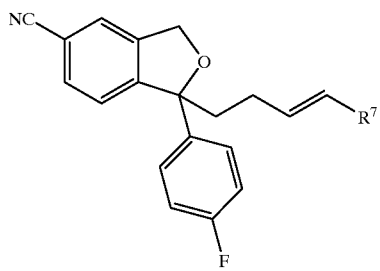

(X)

wherein R$^7$ is as defined above, which is oxidised to form a compound of formula

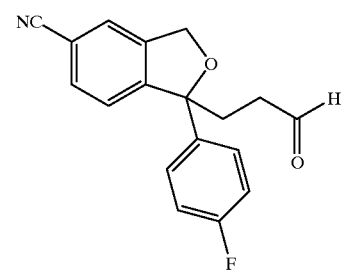

(XI)

followed by reductive amination with dimethylamin to form citalopram.

In a eight embodiment, the invention relates to a process for the preparation of citalopram wherein the compound of formula (I) is reacted with a compound of formula (II) wherein R is —CH$_2$—Me(Pg$_1$) followed by removal of the protection group to form a compound of formula

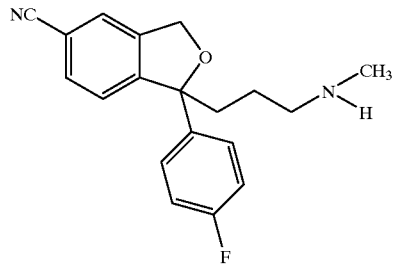

(XII)

and thereafter methylation of the amino group or reductive amination to form citalopram.

In a final embodiment, the invention relates to a method for the preparation of citalopram wherein the compound of formula (I) is reacted with a compound of formula (II) wherein R is —CO—NHR$^8$ wherein R$^8$ is hydrogen or methyl, followed by reduction of the resulting compound of the formula

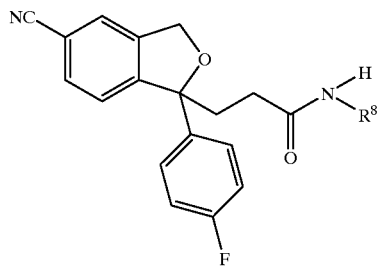

(XIII)

wherein R$^8$ is as defined above, to form a compound of formula

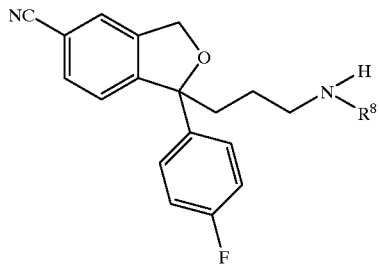

(XIV)

wherein R$^8$ is as defined above, followed by methylation or reductive amination to form citalopram.

In another aspect, the present invention provides the novel intermediates of the general formula (III), (IV), (VI), (XI) and (XII).

In yet another aspect, the present invention relates to an antidepressant pharmaceutical composition comprising citalopram manufactured by the process of the invention.

The alkylation step where the compound of formula (I) is reacted with a compound of formula (II) is suitably carried out by treatment of the compound of formula (I) with a base such as for example LDA ( lithiumdiisopropylamine), LiH- MDS (hexamethyldisilasan lithium), NaH, NaHMDS (hexamethyldisilasan sodium) and metalalkoxides such as NaOMe, KOMe, LiOMe, NaOtertBu, KOtertBu and LiOtertBu in an aprotic organic solvent such as THF (tetrahydrofurane), DMF (dimethylformamide), NMP (N-methylpyrrolidon), ethers such as diethylether or dioxalane, toluene, benzene, or alkanes and mixtures thereof. The anion formed is then reacted with a compound of formula (II) whereby a group of formula $-CH_2-CH_2-R$ is introduced into position 1 of the isobenzofuranyl ring system.

Leaving groups X, may be a halogenide or a sulphonate of formula $-O-SO_2-R^0$ wherein $R^0$ is alkyl, or optionally alkyl substituted aryl or aralkyl. Suitably, $R^0$ is methyl or p-methylphenyl.

The substituents $R^1$ and $R^2$ are preferably alkyl, or aralkyl or $R^1$ and $R^2$ together form a chain of 2 to 4 carbon atoms. Suitably, $R^1$ and $R^2$ are identical.

The substituents $R^3$, $R^4$, $R^5$ and $R^6$ are preferably alkyl, or aralkyl. Suitably, $R^4$, $R^5$ and $R^6$ are identical.

$R^7$ is preferably alkyl or aralkyl.

The alcohol protecting group Pg may be a trialkylsilyl group, a benzyl group or a tetrahydropyranyl group (THP).

According to the invention, the alcohol protecting group is removed to form the compound of formula (IV) using conventional methods for removal of the protection group in question.

Thus, where the protecting group is trialkylsilyl the protecting group may be removed by treatment with a base, an organic or mineral acid or a flouride such as KF or trialkylaminoflouride.

Where Pg is benzyl, the protecting group may be removed by reduction using Pd/C or Pt/C as a catalyst.

Where Pg is a tetrahydropyranyl (THP) group, the protecting group may be removed by treatment with an organic or mineral acid, or resins carrying H$^+$ groups such as Dowex H$^+$ or Amberlyst.

The alcohol group in the compound of formula (IV) is converted to a feasible leaving group such as halogen, or a sulphonate of formula $-O-SO_2-R^0$ wherein $R^0$ is as defined above, by reaction with reagents such as thionylchloride, mesylchloride, tosylchloride, etc.

The resulting compound is then reacted with dimethylamin or a metal salt thereof, e.g. M$^+$, $^-$N(CH$_3$)$_2$ wherein M$^+$ is Li$^-$ or Na$^+$. The reaction is suitably carried out in an aprotic organic solvent such as THF (tetrahydrofurane), DMF (dimethylformamide), NMP (N-methyl pyrrolidon), ethers such as diethylether, or dioxalane, toluene, benzene, or alkanes and mixtures thereof. The compound of formula (IV) carrying a suitable leaving group may also be converted to citalopram by reaction with dimethylammonium chloride in presence of a base. Alternatively, the compound of formula (IV) carrying a suitable leaving group, such as a sulphonate of formula $-O-SO_2-R^0$ wherein $R^0$ is as defined above, may be reacted with an azide, such as sodium azide, followed by reduction using Pd/C as a catalyst to form a compound of formula (VI) and thereafter methylation or reductive amination to form Citalopram.

The compound of formula (IV) carrying a suitable leaving group, may also be converted to citalopram by reaction with methylamine to form a compound of formula (XII) above, followed by methylation or reductive amination to form Citalopram.

The reduction of the amide of formula (V) is conveniently carried out in toluene using Red-Al as a reducing agent.

Suitable groups Pg$_1$ and Pg$_2$ are aralkyl or $-O-SO_2-R^0$ groups wherein $R^0$ is as defined above, typically benzyl or tosyl, or Pg$_1$ and Pg$_2$ together with the N atom to which they are attached form an optionally substituted phthalimide group.

The protecting groups, Pg$_1$ and Pg$_2$ may be removed using conventional methods for removal of such protective groups. The phthalimide groups may thus be converted to an amino group by treatment with hydrazin or methylamine and ethanol.

Where the protecting group is an aralkyl group, such as benzyl, it may be removed by reduction, typically in presence of Pd/C or Pt/C as a catalyst.

The sulphonate groups of formula $-O-SO_2-R^0$ may be removed by treatment with Red-Al.

The free amino group in the compound of formula (VI) may be methylated with methylating agents such as MeI and Me$_2$SO$_4$, wherein Me is methyl. The methylation is carried out using conventional procedures for carrying out such reactions.

Alternatively, citalopram is formed by reductive amination. According to this procedure, the compound of formula (VI) is reacted with compounds such as formaldehyde, paraformaldehyde or trioxan in presence of a reducing agent such as NaBH$_4$ or NaBH$_3$CN. The reductive amination is carried out using conventional procedures for carrying out such reactions.

The compound of formula (VIIa) or (VIIb) may suitably be converted to the corresponding aldehyde by treatment with an organic or mineral acid or with resins carrying H$^+$ groups such as Dowex H$^+$ or Amberlyst.

The resulting aldehyde may be converted to citalopram by reductive amination, i.e. by reaction with dimethylamine in the presence of a reducing agent such as NaBH$_4$ or NaBH$_3$CN. Dimethylamine may be added to the reaction in the form of the dimethylammonium chloride salt.

The ester derivative of formula (VIII) may be converted to citalopram via the corresponding alcohol of formula (IV) by reduction of the ester using Red-Al as a reducing agent or via the corresponding amide of formula (V) by reaction of the ester with NH(Me)$_2$ or a metal salt thereof.

Suitable, the agent useful for conversion of a compound of formula (IX) to a compound of formula (VI) is NaOH/Br$_2$.

Oxidation of the compound of formula (X) may be carried out by treatment of the compound with ozone in a polar solvent such as alcohol, water, acetic acid or esters thereof. Alternatively, the compound of formula (X) may be treated with oxidation agents such as NaIO$_4$, OsO$_4$/NaIO$_4$ and KMnO$_4$.

The reductive amination of a compound of formula (XI) may suitably be carried out by reaction with dimethylamin in presence of a reducing agent such as NaBH$_4$ or NaBH$_3$CN. Dimethylamine may be added to the reaction in the form of dimethylammonium chloride.

The amino group in the compounds of formula (XII) and (XIV) may be methylated with methylating agents such as MeI and Me$_2$SO$_4$, wherein Me is methyl. The methylation is carried out using conventional procedures for carrying out such reactions.

Alternatively, the amino group in the compounds of formula (XII) and (XIV) may be methylated by reductive amination. According to this procedure, the compound of formula (XII) or (XIV) is reacted with compounds such as formaldehyde, paraformaldehyde or trioxan in presence of a reducing agent such as NaBH$_4$ or NaBH$_3$CN. The reductive amination is carried out using conventional procedures for carrying out such reactions.

The reaction conditions, solvents, etc. used for the reactions described above are conventional conditions for such reactions and may easily be determined by a person skilled in the art.

The starting material of formula (I) may be prepared as described in U.S. Pat. No. 4,136,193 or as described in WO 98/019511.

The compounds of formula (II) are commercially available or may be prepared from commercially available starting materials using conventional techniques.

Citalopram is on the market as an antidepressant drug in the form of the racemate. However, in the near future the active S-enantiomer of citalopram is also going to be introduced to the market.

S-citalopram may be prepared by separation of the optically active isomers by chromatography.

Throughout the specification and claims, the term alkyl refers to a branched or unbranched alkyl group having from one to six carbon atoms inclusive, such as methyl, ethyl, 1-propyl, 2-propyl, 1-butyl, 2-butyl, 2-methyl-2-propyl, 2,2-dimethylethyl and 2- methyl-1-propyl.

Similarly, alkenyl and alkynyl, respectively, designate such groups having from two to six carbon atoms, including one double bond or triple bond respectively, such as ethenyl, propenyl, butenyl, ethynyl, propynyl and butynyl.

The term aryl refers to a mono or bicyclic carbocyclic aromatic group, such as phenyl and naphthyl, in particular phenyl.

The term aralkyl refers to aryl-alkyl, wherein aryl and alkyl is as defined above.

Optionally alkyl substituted aryl and aralkyl refers to aryl and aralkyl groups which may optionally be substituted with one or more alkyl groups.

Halogen means chloro, bromo or iodo.

Citalopram may be used as the free base, in particular the free base in crystalline form, or as a pharmaceutically acceptable acid addition salt thereof. As acid addition salts, such salts formed with organic or inorganic acids may be used. Exemplary of such organic salts are those with maleic, fumaric, benzoic, ascorbic, succinic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, paminobenzoic, glutamic, benzene sulfonic and theophylline acetic acids, as well as the 8halotheophyllines, for example 8bromotheophylline. Exemplary of such inorganic salts are those with hydrochloric, hydrobromic, sulfuric, sulfamic, phosphoric and nitric acids.

The acid addition salts of the compounds may be prepared by methods known in the art. The base is reacted with either the calculated amount of acid in a water miscible solvent, such as acetone or ethanol, with subsequent isolation of the salt by concentration and cooling, or with an excess of the acid in a water immiscible solvent, such as ethylether, ethylacetate or dichloromethane, with the salt separating spontaneously.

The pharmaceutical compositions of the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting maschine. Examples of adjuvants or diluents comprise: Corn starch, potato starch, talcum, magnesium stearate, gelatine, lactose, gums, and the like. Any other adjuvant or additive, colourings, aroma, preservatives etc. may be used provided that they are compatible with the active ingredients.

Solutions for injections may be prepared by solving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

The invention is further illustrated by the following examples.

EXAMPLE 1

A solution of 1-(4-fluorophenyl)-1,3-dihydroisobenzofuran-5-carbonitrile (4.8 g, 0.02 mol) in THF (50 mL) was added dropwise to a solution of LDA (Butyl lithium 1.6M (15 mL), disopropylamine 2.6 g) at −30° C. under an atmosphere of nitrogen. After stirring at −30° C. for 10 minutes a solution of the alkyl halide (0.02 mol) in THF (25 mL) was added dropwise and allowed to warm to room temperature and stirred for a further 60 minutes. The reaction was then quenched with ice, extracted with toluene (3×50 mL), washed with water (50 mL) and concentrated under reduced pressure. The residue was purified by chromatography on silica gel using mixtures of n-heptane/EtOAc as the eluent. The resulting anion is then reacted with a compound of formula (II).

EXAMPLE 2

Preparation of 1-[(3-benzyloxy)propyl]-1-(4-fluorophenyl)-1,3-dihydro-5-isobenzofurancarbonitrile:

A solution of 1-(4-fluorophenyl)-1,3-dihydro-5-isobenzofurancarbonitrile (2.2 g, 9.2 mmol) in THF (40 mL) was added to a solution of LDA (12 mmol) in THF (70 mL) at −78° C. under an atmosphere of nitrogen. After stirring at −78° C. for 30 min, a solution of benzyl-3-bromopropylether (2 mL., 12 mmol) in THF (10 mL) was added and the resulting mixture was allowed to warm to room temperature and stirred for 2 h. Then the mixture was poured into ice/$H_2O$ (100 mL) and extracted with $Et_2O$ (3×150 mL). The organic extracts were washed with $H_2O$ (100 mL) and brine (100 mL), dried and evaporated. Silica gel chromatography (heptane, EtOAc 5:1) of the residue gave the product as an oil (2.0 g, 60%). $^1$H NMR (DMSO-$d_6$) δ1.35 (1H, m); 1.45 (1H, m); 2.23 (2H, m); 3.38 (2H, dd, J=5.5 and 6.6 Hz)); 4.38 (2H, s); 5.14 (1H, d, J=13.7 Hz); 5.19 (1H, d, J=13.7 Hz); 7.15 (2H, t, J=8.8 Hz); 7.25 (3H, J=7.27 Hz); 7.32 (2H, m); 7.58 (2H, dd, J=5.6 and 8.8 Hz); 7.75 (3H, m).

Preparation of 1-(4-fluorophenyl)-1-[3-(tetrahydropyranyloxy)propyl]-1,3-dihydro-5-isobenzofurancarbonitrile:

The same procedure was used to give the title compound as an oil (2.0 g, 60%). $^1$H NMR (DMSO-$d_6$)δ1.40 (6H, m); 1.52 (1H, m); 1.65 (1H, m); 2.20 (2H, m); 3.30 (1H, m); 3.38 (1H, m); 3.55 (1H, m); 3.65 (1H, m); 4.45 (1H, dd); 5.15 (1H, d, J=13.0 Hz); 5.19 (1H, d, J=13.0 Hz); 7.15 (2H, t, J=8.8 Hz); 7.58 (2H, dd, J=5.7 and 9.0 Hz); 7.75 (1H, d, J=8.0 Hz); 7.79 (2H, s+d, J=8.0 Hz).

EXAMPLE 3

Preparation of 1-(4-fluorophenyl)-1-(3-hydroxypropyl)-1,3-dihydro-5-isobenzofurancarbonitrile:

(i) A solution of 1-(4-fluorophenyl)-1,3-dihydro-5-isobenzofurancarbonitrile (13.4 g, 60 mmol) in THF (450 mL) was added to a solution of LDA (76 mmol) in THF (30 mL) at −78° C. under an atmosphere of nitrogen. After stirring at −78° C. for 30 min, a solution of (3-bromopropoxy)-tert-butyldimethylsilane (16.8 mL, 72 mmol) in THF (30 mL) was added and the resulting mixture was allowed to warm to room temperature and stirred for 2 h. Then the mixture was poured into ice/H$_2$O (400 mL), and extracted with Et$_2$O (3×500 mL). The organic extracts were washed with H$_2$O (500 mL) and brine (500 mL), dried and evaporated. The residue was dissolved in methanol (400 mL) and was added 1M HCl (200 mL). The resulting solution was stirred at room temperature for 1 h and evaporated. Silica gel chromatography (heptane, EtOAc 5:1) of the residue gave the title product as an oil (14.4 g, 81%). $^1$H NMR (DMSO-d$_6$) δ1.25 (2H, m); 2.18 (2H, t, J=8.8 Hz); 3.31 (2H, q, J=6.2 Hz); 4.34 (1H, t, J=6.2 Hz); 5.12 (1H, d, J=13.2 Hz); 5.17 (1H, d, J=13.2 Hz); 7.15 (2H, t, J=8.8 Hz); 7.58 (2H, dd, J=6.0 and 8.8 Hz); 7.72 (1H, s); 7.78 (2H, br d, J=6.0 Hz.). $^{13}$C NMR (DMSO-d—$_6$) δ27.4; 37.3; 59.8; 71.0; 90.7; 110.5; 114.8; 115.2; 118.8; 123.2; 125.6; 126.9; 127.1; 132.0; 139.9; 140.6; 149.5; 160.9; 162.0.

(ii) To a solution of 1-[(3-benzyloxy)propyl]-1-(4-fluorophenyl)-1,3-dihydro-5-isobenzofurancarbonitrile (1.2 g, 3.1 mmol) and 1,4-cyclohexadiene (5.5 mL, 58.1 mmol) in ethanol (50 mL) was added Pd/C (4 g, 5%). The reaction mixture was refluxed under a nitrogen atmosphere for 2 days, then cooled to room temperature and filtered through Celite. The filtrate was evaporated and the residue was purified by silica gel chromatography to give the title product as an oil (0.75 g, 80%). $^1$H NMR (CDCl$_3$)δ1.5 (2H, m); 2.25 (2H, m); 3.5 (2H, t); 5.2 (2H, dd); 7.05 (2H, t, J=10.0 Hz); 7.41 (3H, m); 7.49 (1H, br s); 7.56 (2H, J=7.0 Hz).

(iii) To a solution of 1-(4-fluorophenyl)-1-[3-(tetrahydropyranyloxy)propyl]-1,3-dihydro-5-isobenzofurancarbonitrile (1.5 g, 4.1 mmol) in methanol was added catalytic amount of p-toluenesulfonic acid monohydrate (60 mg) and the resulting mixture was stirred at room temperature for 1 h and then evaporated. Silica gel chromatography (heptane, EtOAc 5:1) gave the title product (1.0 g, 91%). $^1$H NMR (CDCl$_3$) was identical with that obtained from 1-[(3-benzyloxy)propyl]-1-(4-fluorophenyl)-1,3-dihydro-5-isobenzofurancarbonitrile.

EXAMPLE 4

Preparation of 1-(4-fluorophenyl)-1-[(3-p-toluenesulfonyloxy)propyl]-1,3-dihydro-5-isobenzofurancarbonitrile:

To a solution of 1-(4-fluorophenyl)-1-(3-hydroxypropyl)-1,3-dihydro-5-isobenzofurancarbonitrile (2.5 g, 8.4 mmol) in toluene (50 mL) at 0–5° C. were added triethylamine (2.5 mL, 18.0 mmol) and a solution of p-toluenesulfonyl chloride (2.6 g, 13.6 mmol) in toluene (10 mL). The resulting mixture was stirred at room temperature for 3 days, then washed with H$_2$O and saturated aqueous NaHCO$_3$ solution. Evaporation of the organic extract followed by silica gel chromatography (heptane, EtOAc 4:1) of the residue gave the title product as an oil (1.6 g, 42%). $^1$H NMR (CDCl$_3$) δ1.6 (2H, m); 2.15 (2H, m); 2.45 (3H, s); 4.05 (2H, t, J=8.0 Hz); 5.15 (2H, s); 7.05 (2H, t, J=8.5 Hz); 7.30–7.42 (5H, m); 7.50 (1H, s); 7.6 (1H, d, J=7.5 Hz); 7.75 (2H, d, J=7.5 Hz).

EXAMPLE 5

Preparation of 1-(4-fluorophenyl)-1-[(3-methanesulfonyloxy)propyl]-1,3-dihydro-5-isobenzo furan-carbonitrile:

To a solution of 1-(4-fluorophenyl)-1-(3-hydroxypropyl)-1,3-dihydro-5-isobenzofurancarbonitrile (14.4 g, 50.0 mmol) in THF (500 mL) at 0–5° C. were added triethylamine (30 mL, 41.8 mmol) and a solution of methanesulfonyl chloride (11.6 mL, 150 mmol) in THF (20 mL). The resulting mixture was stirred at room temperature overnight, then added toluene (200 mL) and washed with H$_2$O and saturated aqueous NaHCO$_3$ solution. Evaporation of the organic phase followed by silica gel chromatography (heptane, EtOAc 3:1) of the residue gave the title product as an oil (12.0 g, 64%). $^1$H NMR (CDCl$_3$) δ1.70 (2H, m); 2.25 (2H, m); 2.90 (3H, s); 4.22 (2H, t, J=7.0 Hz); 5.14 (1H, d, J=13.2 Hz); 5.14 (1H, d, J=13.2 Hz); 7.01 (2H, t, J=9.0 Hz); 7.41 (2H, d; J=9.0 Hz); 7.45 (1H, d, J=8.0 Hz); 7.52(1H, s); 7.61 (1H, br d, J=8.0 Hz).

EXAMPLE 6

Preparation of 1-[3-(N,N-dimethylamino)propyl]-1-(4-fluorophenyl)-1,3-dihydro-5-isobenzofurancarbonitrile, (Citalopram, Oxalate):

To a solution of 1-(4-fluorophenyl)-1-[(3-p-toluenesulfonyloxy)propyl]-1,3-dihydro-5-isobenzofurancarbonitrile (0.20 g, 0.4 mmol) in DMF (10 mL) was added triethylamine (1.4 mL, 7.0 mmol) and dimethylammonium chloride (0.41 g, 5.0 mmol). The reaction mixture was stirred at 70° C. overnight, then cooled to room temperature, poured into ice/H$_2$O and extracted with Et$_2$O (3×30 mL). The organic extracts were washed with H$_2$O and brine, and evaporated. The residue was purified by silica gel chromatography (heptane, EtOAc, triethylamine 1:3:4%) and crystallised from acetone as the oxalate salt (0.12 g, 70%). DSC (open chamber), T$_{onset}$=158.96, T$_{peak}$=162.14. $^1$H NMR (DMSO-d$_6$) δ1.42 (1H, m); 1.51 (1H, m); 2.22 (2H, t, J=8.0 Hz); 2.62 (6H, s); 2.95 (2H, t, J=8.0 Hz); 5.15 (1H, d, J=14.0 Hz); 5.23 (1H, d, J=14.0 Hz); 7.18 (2H, t, J=9.0 Hz); 7.59 (2H, dd, J=5.0 and 8.0 Hz); 7.74 (1H, d, J=7.5 Hz); 7.79 (1H, d, J=7.0 Hz); 7.80 (1H, br s). $^{13}$C NMR (DMSO-d$_6$)δ19.3; 37.0; 42.3; 56.7; 71.2; 90.3; 110.7; 115.2; 115.3; 118.8; 123.2; 125.8; 127.0; 132.1; 139.9; 140.0; 148.161.4; 164.3. Anal. (C$_{20}$H$_{21}$N$_2$O, C$_2$H$_2$O$_4$) calcd. C: 63.76; H:5.59; N:6.76. Found C:63.50; H:5.78; N:6.63.

EXAMPLE 7

Preparation of 1-[3-(N,N-dimethylamino)propyl]-1-(4-fluorophenyl)-1,3-dihydro-5-isobenzofurancarbonitrile, (Citalopram, Oxalate):

Dimethylamine (18 mL, 100 mmol, 33% in ethanol) was added to a solution of 1-(4-fluorophenyl)-1-[(3-methanesulfonyloxy)propyl]-1,3-dihydro-5-isobenzofurancarbonitrile (1.0 g, 2.7 mmol) in ethanol (10 mL) and THF (20 mL). The resulting mixture was stirred at room temperature for 1 h and at 60° C. for 3 h. After cooling, the reaction mixture was evaporated. 1M NaOH (70 mL) was added to the residue and extracted with Et$_2$O (100 mL). The organic extract was washed with brine, dried and evaporated. The residue was filtered through silica gel (EtOAc, heptane, triethylamine 75:25:1) and crystallised from acetone as the oxalate salt (0.72 g, 65%). DSC (open chamber), T$_{onset}$=158.56, T$_{peak}$=161.59. The NMR-spectra were identical with those obtained from citalopram. oxalate prepared in example 6. Anal. (C$_{20}$H$_{21}$N$_2$O, C$_2$H$_2$O$_4$) calcd. C: 63.76; H: 5.59; N: 6.76. Found C: 63.57; H: 5.51; N: 6.77.

EXAMPLE 8

Preparation of 1-(4-fluorophenyl)-1-[3-(phthalimidopropyl)]-1,3-dihydro-5-isobenzofurancarbonitrile:

A solution of 1-(4-fluorophenyl)-1,3-dihydro-5-isobenzofurancarbonitrile (4.4 g, 20 mmol) in THF (40 mL)

was added to a solution of LDA (24 mmol) in THF (70 mL) at −78° C. under an atmosphere of nitrogen. After stirring at −78° C. for 30 min, a solution of 2-(3-brompropyl) phthalimide (6.4 g, 24 mmol) in THF (20 mL) was added and the resulting mixture was allowed to warm to room temperature and stirred for 5 h. Then the mixture was poured into ice/$H_2O$ (200 mL), and extracted with $Et_2O$ (3×250 mL). The organic extracts were washed with $H_2O$ (100 mL) and brine (100 mL) dried and evaporated. Silica gel chromatography (heptane, EtOAc 5:1) of the residue gave the product as a yellow powder (3.0 g, 36%). A sample was recrystallised from ethanol. $^1H$ NMR ($CDCl_3$)δ1.69 (1H, m); 1.74 (1H, m); 1.93 (1H, m); 3.08 (1H, dt, J=4.7 and 12.2 Hz); 3.85 (1H, ddd, J=1.4 and 7.1 and 11.8 Hz); 4.08 (1H, ddd, J=4.2 and 10.8 and 17.9 Hz); 5.09 (1H d, J=13.1 Hz); 5.20 (1H, d, J=13.1); 6.60 (1H, d, J=7.5 Hz); 7.06 (2H, t, J=9.4 Hz); 7.28 (1H, t, J=7.5 Hz): 7.42 (1H, t, J=7.5 Hz); 7.43 (1H, s); 7.58 (1H, d, J=8.0 Hz); 7.77 (1H, d, J=7.5 Hz); 7.80 (1H, t, J=5.2 Hz); 7.95 (1H d, J=8.0 Hz). $^{13}C$ NMR ($CDCl_3$) δ23.4; 31.8; 59.3; 72.6; 92.3; 112.6; 114.7; 118.2; 122.9; 123.7; 124.8; 125.2; 129.0; 131.1; 131.6; 132.9; 135.8; 140.9; 144.1; 145.6; 161.6; 163.6; 170.9. Anal. ($C_{26}H_{19}FN_2O_3$, ½ $C_2H_5OH$) calcd. C: 72.15; H: 4.93; N: 6.23. Found C: 72.66; H: 5.14; N: 6.09.

EXAMPLE 9

Preparation of 1-(3-Azidopropyl)-1-(4-fluorophenyl)-1,3-dihydro-5-isobenzofurancarbonitrile:

Sodium azide (5.5 g, 80.5 mmol) was added to a solution of 1-(4-fluorophenyl)-1-[(3-methanesulfonyloxy)propyl]-1,3-dihydro-5-isobenzofurancarbonitrile (4.0 g, 10.6 mmol) in DMF (100 mL). The resulting mixture was stirred at 40° C. for 3 h, and then refluxed for 2 h. After cooling the reaction mixture was poured into $H_2O$ and extracted with $Et_2O$ (4×200 mL). The organic extracts were washed with $H_2O$ and brine, dried and evaporated to give the crude product as a brown oil (1.3 g, 45%). $^1H$ NMR (DMSO-$d_6$)δ1.40 (2H, m); 2.22 (2H, m); 3.30 (2H, t, J=6.6 Hz); 5.10 (1H, d, J=13.7 Hz); 5.21 (1H, d, J=13.7 Hz); 7.18 (2H, t, J=8.5 Hz): 7.59 (2H, dd, J=5.2 and 8.5 Hz); 7.78 (3H, s+d, J=8.1 Hz).

Preparation of 1-(3-Aminopropyl)-1-(4-fluorophenl)-1,3-dihydro-5-isobenzofurancarbonitrile:

A mixture of 1-(3-azidopropyl)-1-(4-fluorophenyl)-1,3-dihydro-5-isobenzofurancarbonitrile (1.3 g, 4.4 mmol) and palladium on carbon (0.6 g, 5%) in ethanol (50 mL) was hydrogenated for 2 h. The mixture was filtered through Celite and evaporated to give the crude product as a brown oil (0.8 g, 66%). $^1H$ NMR (DMSO-$d_6$)δ1.11 (1H, m); 1.22 (1H, m); 2.12 (2H, m); 2.48 (2H, t, J=7.1 Hz); 5.15 (1H, d, J=13.7 Hz); 5.19 (1H, d, J=13.7 Hz); 7.15(2H, t, J=8.9 Hz); 7.58 (2H, dd, J=5.2 and 8.5 Hz); 7.72 (1H, d, J=8.4 Hz); 7.78 (2H, s+d, J=8.1 Hz).

Preparation of 1-[3-(N,N-Dimethylamino)propyl]-1-(4-fluoroplenyl)-1,3-dihydro-5-isobenzofurancarbonitrile, (Citalopram, Oxalate):

Sodium cyanoborohydride (0.34 g, 5.4 mmol) was added to a mixture of 1-(3-Aininopropyl)-1-(4-fluorophenyl)-1,3-dihydro-5-isobenzofurancarbonitrile (0.80 g, 2.7 mmol) and formaldehyde (0.44 mL, 5.4 mmol, 37% in $H_2$0) in methanol (10 mL). The resulting mixture was stirred at room temperature for 3 h, then was added more sodium cyanoborohydride (0.17 g, 2.7 mmol) and formaldehyde (0.22 mL, 2.7 mmol). After stirring at room temperature for 1 h, the mixture was quenched with $H_2O$ and extracted with $Et_2O$. The organic extracts were dried and evaporated. Silica gel chromatography (EtOAc, heptane, triethylamine 75:25:1) of the residue gave the crude product, which was isolated as the oxalate salt from acetone (0.31 g 0.8 mmol, 30%). The NMR-spectra were identical with those obtained from citalopram oxalate prepared in example 6. Anal. ($C_{20}H_{21}N_2O$, $C_2H_2O_4$, ¼$H_2O$ ) calcd. C: 63.06; H: 5.67; N: 6.69. Found C: 63.28; H: 5.64; N: 6.67.

EXAMPLE 10

Preparation of 1-(4-fluorophenyl)-1-[3-(N-methylamino) propyl]-1,3-dihydro-5-isobenzofurancarbonitrile, Oxalate Salt:

The compound was prepared from methylamine (60 mL, 120 mmol, 2M solution in THF) using the method described in example 7. Yield: 760 mg, 36%. $^1H$ NMR (DMSO-$d_6$) δ1.40 (1H, m); 1.41 (1H, m); 2.25 (2H, t); 2.47 (3H, s); 2.83 (2H, t, J=8.0 Hz); 5.15 (1H, d, J=13.2 Hz); 5.21 (1H, d, J=13.2 Hz); 7.18 (2H, t, J=9.0 Hz); 7.59 (2H, dd, J=5.6 and 7.5 Hz); 7.73 (1H, d, J=8.1 Hz); 7.81 (3H, d+s, J=8.1 Hz).

Preparation 1-[3-(N,N-Dimethylamino)propyl]-1-(4-fluorophenyl)-1,3-dihydro-5-isobenzofurancarbonitrile, (Citalopram, Oxalate):

A solution of 1-[3-(N-methyl-ammonium)propyl]-1-(4-fluorophenyl)-1,3-dihydro-5-isobenzofurancarbonitrile (0.70 g, 2.24 mmol) and formaldehyde (0.5 mL, 6.7 mmol, 37% aqueous solution) in 98% formic acid (5 mL) was refluxed for 4 h. After cooling, 4M HCl (2 mL) was added and the resulting mixture was evaporated. 1M NaOH (50 mL) was added to the residue and extracted with $Et_2O$ (3×100 mL). The organic extract was washed with brine, dried and evaporated. The oxalate salt was isolated from acetone (0.22 g, 30%). DSC (open chamber), $T_{onset}$=157.73, $T_{peak}$=160.80. The NMR-spectra were identical with those obtained from citalopram oxalate prepared in example 6. Anal. ($C_{20}H_{21}N_2O$, $C_2H_2O_4$, ¼ $H_2O$) calcd. C: 63.06; H: 5.67; N: 6.69. Found C: 63.24; H: 5.65; N: 6.62.

EXAMPLE 11

Preparation of 1-[3-([1,3]dioxolan-2-yl)ethyl)-1-(4-fluorophenyl)-1,3-dihydro-5-isobenzofurancarbonitrile:

A solution of 1-(4-fluorophenyl)-1,3-dihydro-5-isobenzofurancarbonitrile (4.46 g, 18.7 mmol) in THF (40 mL) was added to a solution of LDA (24 mmol) in THF (100 mL) at −78° C. under an atmosphere of nitrogen. After stirring at −78° C. for 30 min, a solution of 2-2-(2-bromoethyl)-[1,3]-dioxolane (2.8 mL, 24 mmol) in THF (20 mL) was added and the resulting mixture was allowed to warm to room temperature and stirred for 2 h. Then the mixture was poured into ice/$H_2O$ (100 mL), and extracted with $Et_2O$ (3×300 mL). The organic extracts were washed with $H_2O$ (100 mL) and brine (100 mL), dried and evaporated. Silica gel chromatography (heptane, EtOAc 5:1) of the residue gave the product as an oil (5.5 g, 86%). $^1H$ NMR ($CDCl_3$) δ1.52 (1H, m); 1.70 (1H, m); 2.28 (2H, m); 3.81 (2H, m); 3.89 (2H, m); 4.85 (1H, t, J=4.0 Hz); 5.14 (1H, d, J=13.2 Hz); 5.19 (1H, d, J=13.2 Hz); 7.04 (2H, t, J=8.5 Hz); 7.41 (3H, m); 7.49 (1H, s); 7.58 (1H, d, J=8.0 Hz). $^{13}C$ NMR ($CDCl_3$) δ27.8; 34.4; 64.2; 70.6; 90.1; 103.2; 111.2; 114.5; 114.8; 117.9; 122.2; 124.5; 126.1; 126.2; 131.2; 138.7; 139.7; 148.5; 159.0.

Preparation of 1-(4-fluorophenyl)-1-(3-formylethyl)-1,3-dihydro-5-isobenzofurancarbonitrile:

A solution of 1-[3-([1,3]dioxolan-2-yl)ethyl)-1-(4-fluorophenyl)-1,3-dihydro-5-isobenzofurancarbonitrile (5.30 g, 16 mmol) in 30% aqueous acetic acid (200 mL) was refluxed for 5 h. The reaction mixture was cooled and extracted with CH$_2$Cl$_2$(3×400 mL). The organic extracts were dried and evaporated to give the crude product (5.0 g, contained about 8.0 mmol of the product as judged by NMR and HPLC, 50%), which was used in the next step without further purification. $^1$H NMR (CDCl$_3$) δ1.49 (1H, m); 1.61 (1H, m); 2.38 (1H, m); 2.51 (1H, m); 5.15 (2H, br s); 7.01 (2H, t, J=8.0 Hz); 7.41 (3H, dd+s, J=5.6 and 8.0 Hz); 7.51 (2H, d, J=8.0 Hz); 7.61 (2H, d, J=8.0 Hz).

Preparation of 1-[3-(N,N-dimethylamino)propyl]-1-(4-fluorophenyl)-1,3-dihydro-5-isobenzofurancarbonitrile, (Citalopram, Oxalate):

Sodium cyanoborohydride (0.76 g, 14.4 mmol) was added to a mixture of crude 1-(3-formylethyl)-1-(4-fluorophenyl)-1,3-dihydro-5-isobenzofurancarbonitrile (5.0 g, contained about 8.0 mmol of the compound as judged by NMR and HPLC) and dimethylammonium chloride (1.17 g, 14.4 mmol) in methanol (50 mL) at 0–5° C. The resulting mixture was stirred at room temperature overnight, then added toluene (100 mL) and EtOAc (100 mL) and washed with H$_2$O (100 mL). The aqueous phase was extracted with Et$_2$O (2×100 mL). The combined organic extracts were dried and evaporated. Silica gel chromatography (heptane, EtOAc, triethylamine 25:25:1) of the residue gave the title compound, which was isolated form acetone as the oxalate salt (2.7 g, 82%). DSC (open chamber), T$_{onset}$=159.55, T$_{peak}$=163.54. The NMR-spectra were identical with those obtained from citalopram oxalate prepared in example 6. Anal. (C$_{20}$H$_{21}$N$_2$O, C$_2$H$_2$O$_4$) calcd. C: 63.76; H: 5.59; N: 6.76. Found C: 63.65; H: 5.69; N: 6.80.

What is claimed is:

1. A method for the preparation of citalopram comprising reacting a compound of formula (I)

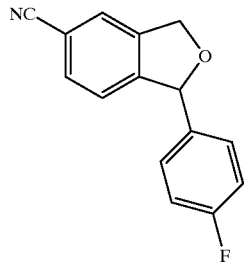

(I)

with a compound having the formula

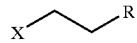

(II)

wherein X is a suitable leaving group and R is —CH$_2$—O—Pg, —CH$_2$—NPg$_1$Pg$_2$, —CH$_2$—NMePg$_1$, —CO—N(CH$_3$)$_2$, —CH(OR$^1$)(OR$^2$), —C(OR$^4$)(OR$^5$)(OR$^6$), —COOR$^3$, —CH$_2$—CO—NH$_2$, —CH=CHR$^7$ or —CO—NHR$^8$, wherein Pg is a protection group for an alcohol group, Pg$_1$ and Pg$_2$ are protection groups for an amino group, R$^1$ and R$^2$ are independently selected from alkyl, alkenyl, alkynyl and optionally alkyl substituted aryl or aralkyl groups or R$^1$ and R$^2$ together form a chain of 2 to 4 carbon atoms, each of R$^3$, R$^4$, R$^5$, R$^6$ and R$^7$ are independently selected from alkyl, alkenyl, alkynyl and optionally alkyl substituted aryl or aralkyl and R$^8$ is hydrogen or methyl;

to form a compound of the formula

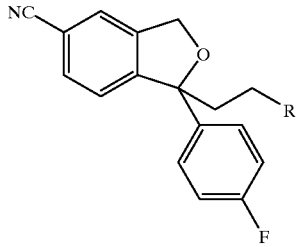

(III)

wherein R is as defined above; followed by conversion of the group R to form a dimethylaminomethyl group and isolation of citalopram base or a pharmaceutically acceptable salt thereof.

2. The method according to claim 1 wherein the compound of formula (I) is reacted with a compound of formula (II) wherein R is —CH$_2$—O—Pg followed by removal of the protection group to form the corresponding alcohol of the formula

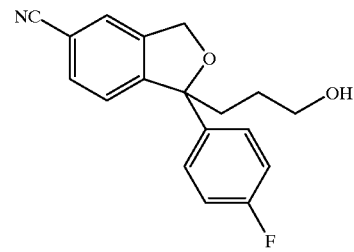

(IV)

and thereafter conversion of the alcohol group to a feasible leaving group and reaction of the resulting compound
 a) with dimethylamine or a metal salt thereof to form citalopram,
 b) with methylamine followed by reductive amination to form citalopram, or
 c) with an azide followed by reduction to form the corresponding amino compound and thereafter methylation or reductive amination to form citalopram.

3. The method according to claim 1 wherein the compound of formula (I) is reacted with a compound of formula (II) wherein R is —CO—N(CH$_3$)$_2$, followed by reduction of the resulting compound of the formula

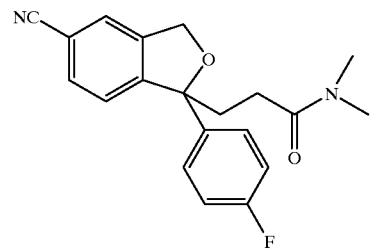

(V)

to form citalopram.

4. The method according to claim 1 wherein the compound of formula (I) is reacted with a compound of formula (II) wherein R is —CH$_2$—N(Pg$_1$)(Pg$_2$) followed by removal of the protection groups to form a compound of formula

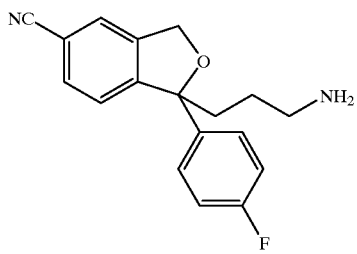

(VI)

and thereafter reductive amination or methylation of the free amino group to form citalopram.

5. The method according to claim 1 wherein a compound of formula (I) is reacted with a compound of formula (II) wherein R is —CH(OR$^1$)(OR$^2$) to form a compound of the formula (VIIa)

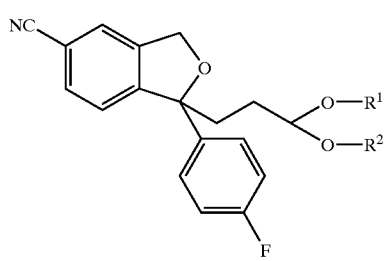

(VIIa)

wherein R$^1$, R$^2$ are as defined above, followed by deprotection of the compound of formula (VIIa) and consecutive reductive amination of the resulting aldehyde to form citalopram.

6. The method according to claim 1 wherein a compound of formula (I) is reacted with a compound of formula (II) wherein R is —COOR$^3$ to form a compound of the formula

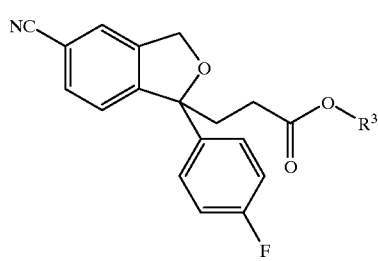

(VIII)

which is converted to an amide of formula (V) followed by reduction to form citalopram, or the compound of formula (VIII) is reduced to form the corresponding alcohol of formula (IV) followed by conversion of the alcohol group to feasible leaving group and consecutively reaction
  a) with dimethylamine or a metal salt thereof to form citalopram,
  b) with methylamine followed by reductive amination to form citalopram, or
  c) with an azide followed by reduction to form the corresponding amino compound and thereafter methylation or reductive amination to form citalopram.

7. The method according to claim 1 wherein a compound of formula (I) is reacted with a compound of formula (II) wherein R is —CH$_2$—CONH$_2$ to form a compound of formula

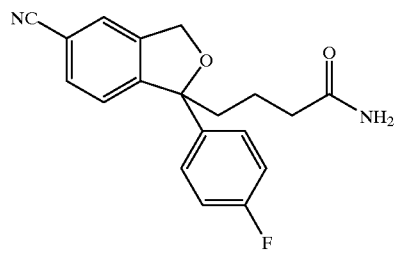

(IX)

which is treated with hypohalide to form a compound of formula

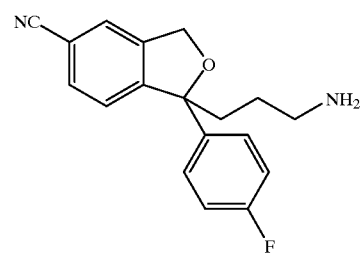

(VI)

followed by methylation of the free amino group or reductive amination to form citalopram.

8. The method according to claim 1 wherein a compound of formula (I) is reacted with a compound of formula (II) wherein R is —CH=CHR$^7$ to form a compound of formula

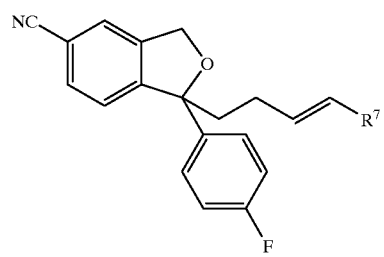

(X)

wherein R$^7$ is as defined above, which is oxidised to form a compound of formula

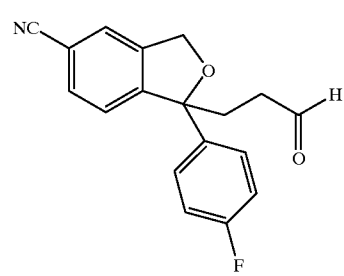

(XI)

followed by reductive amination to form citalopram.

9. The method according to claim 1 wherein the compound of formula (I) is reacted with a compound of formula (II) wherein R is —CH$_2$—Me(Pg$_1$) followed by removal of the protection group to form a compound of formula (XII)

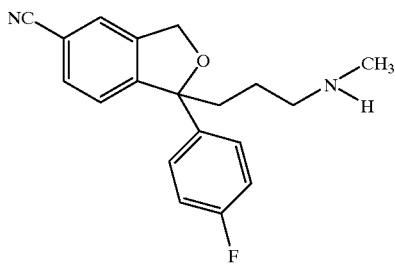

and thereafter methylation of the amino group or reductive amination to form citalopram.

10. The method according to claim 1 wherein the compound of formula (I) is reacted with a compound of formula (II) wherein R is —CO—NHR$^8$ wherein R$^8$ is hydrogen or methyl, followed by reduction of the resulting compound of the formula (XIII)

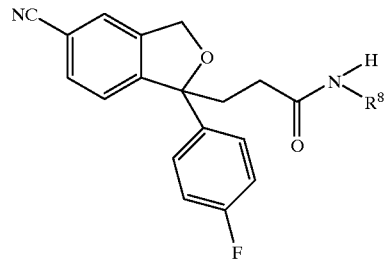

wherein R$^8$ is as defined above, to form a compound of formula (XIV)

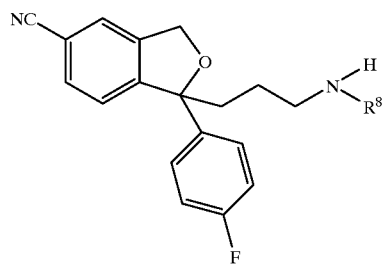

wherein R$^8$ is as defined above, followed by methylation or reductive amination to form citalopram.

11. The method according to claim 1 wherein the reaction of the compound of formula (I) with a compound of formula (II) is carried out in presence of a base selected from LDA (lithiumdiisopropylamine), LiHMDS (hexamethyldisilasan lithium), NaH, NaHMDS (hexamethyldisilasan sodium) and a metalalkoxide.

12. The method of claim 1, wherein said metalalkoxide is selected from the group consisting of NaOMe, KOMe, LiOMe, NaOtertBu, KOtertBu and LiOtertBu.

13. An antidepressant pharmaceutical composition comprising citalopram manufactured by the process of any of claims 1 to 11.

14. A compound having the general formula (III)

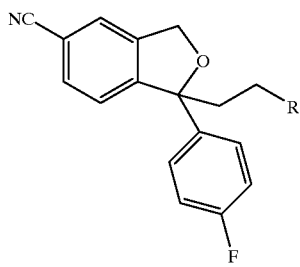

wherein R is —CH$_2$—O—Pg, —CH$_2$—NPg$_1$Pg$_2$, —CH$_2$—NMePg$_1$, —CO—N(CH$_3$)$_2$, —CH(OR$^1$)(OR$^2$), —C(O$^4$)(OR$^5$)(OR$^6$), —COOR$^3$, —CH$_2$CO—NH$_2$, —CH=CHR$^7$ or —CO—NHR$^8$, wherein Pg is a protection group for an alcohol group, Pg$_1$ and Pg$_2$ are protection groups for an amino group, R$^1$ and R$^2$ are independently selected from alkyl, alkenyl, alkynyl and optionally alkyl substituted aryl or aralkyl groups or R$^1$ and R$^2$ together form a chain of 2 to 4 carbon atoms, each of R$^3$, R$^4$, R$^5$, R$^6$ and R$^7$ are independently selected from alkyl, alkenyl, alkynyl and optionally alkyl substituted aryl or aralkyl and R$^8$ is hydrogen or methyl, and acid addition salts thereof.

15. A compound intermediate having the formula (IV)

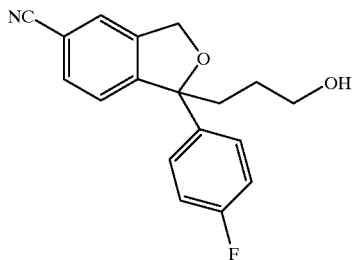

and acid addition salts thereof.

16. A compound having the formula (VI)

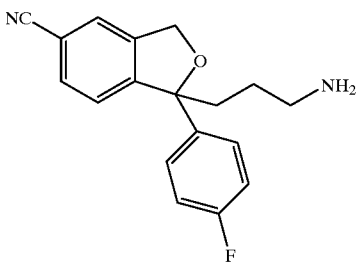

and acid addition salts thereof.

17. A compound having the formula
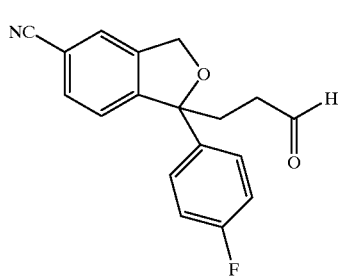
(XI)
and acid addition salts thereof.
18. A compound having the formula
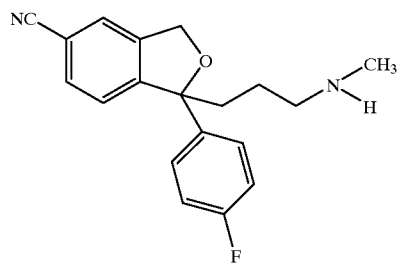
(XII)
and acid addition salts thereof.
* * * * *